United States Patent
Waschkies et al.

(10) Patent No.: US 11,085,903 B2
(45) Date of Patent: Aug. 10, 2021

(54) METHOD, DEVICE AND USE FOR THE DEVICE FOR QUANTITATIVELY DETERMINING THE CONCENTRATION OR PARTICLE SIZE OF A COMPONENT OF A HETEROGENEOUS MATERIAL MIXTURE

(71) Applicants: FRAUNHOFER-GESELLSCHAFT ZUR FÖRDERUNG DER ANGEWANDTEN FORSCHUNG E.V., Munich (DE); NEMAK S.A.B. DE C.V., Garcia N.L. (MX); HYDRO ALUMINIUM ROLLED PRODUCTS GMBH, Grevenbroich (DE); INOSON GMBH, St. Ingbert (DE); RHEINISCH-WESTFÄLISCHE TECHNISCHE HOCHSCHULE (RWTH) AACHEN, Aachen (DE)

(72) Inventors: Thomas Waschkies, Blieskastel (DE); Andrea Reuther, Saarbruecken (DE); Rudolf Licht, Blieskastel (DE); Miriam Weikert-Mueller, Saarbruecken (DE); Friederike Feikus, Aachen (DE); Sebastian Fischer, Frankfurt (DE); Mark Badowski, Bonn (DE); Thomas Hahn-Jose, St. Ingbert (DE)

(73) Assignees: NEMAK S.A.B. DE C.V., Garcia N.L. (MX); HYDRO ALUMINIUM ROLLED PRODUCTS GMBH, Grevenbroich (DE)

( * ) Notice: Subject to any disclaimer, the term of this patent is extended or adjusted under 35 U.S.C. 154(b) by 198 days.

(21) Appl. No.: 16/309,162

(22) PCT Filed: Apr. 6, 2017

(86) PCT No.: PCT/EP2017/058242
§ 371 (c)(1),
(2) Date: Dec. 12, 2018

(87) PCT Pub. No.: WO2017/215807
PCT Pub. Date: Dec. 21, 2017

(65) Prior Publication Data
US 2019/0145939 A1  May 16, 2019

(30) Foreign Application Priority Data
Jun. 14, 2016 (DE) ............. 10 2016 007 173.7

(51) Int. Cl.
*G01N 29/40* (2006.01)
*G01N 33/205* (2019.01)
(Continued)

(52) U.S. Cl.
CPC ............. *G01N 29/40* (2013.01); *G01N 15/02* (2013.01); *G01N 15/06* (2013.01); *G01N 15/10* (2013.01);
(Continued)

(58) Field of Classification Search
CPC ............. G01N 33/205; G01N 2291/0252
See application file for complete search history.

(56) References Cited

U.S. PATENT DOCUMENTS

| 4,287,755 A | 9/1981 | Mansfield |
| 2004/0200269 A1 | 10/2004 | Muller et al. |
| 2013/0104657 A1 | 5/2013 | Lin et al. |

FOREIGN PATENT DOCUMENTS

| DE | 60001951 T2 | 2/2004 |
| EP | 1 194 772 B1 | 4/2003 |
| WO | 2012/004114 A1 | 1/2012 |

OTHER PUBLICATIONS

International Search Report for PCT/EP2017/058242, dated Jun. 1, 2017; English translation submitted herewith (7 pgs.)
(Continued)

*Primary Examiner* — Herbert K Roberts
(74) *Attorney, Agent, or Firm* — Fitch, Even, Tabin & Flannery LLP

(57) ABSTRACT

The invention relates to a method and a device for quantitive determination of a number and size of particulate components contained in a medium flowing along a flow channel. Ultrasonic waves are coupled into the flowing medium, which are reflected at least partially by the particulate components and reflected ultrasonic wave portions which are detected in a ultrasonic time signals, on which the quantitive determination is based. Amplitude values associated with the individual ultrasonic time signals, are detected which are each greater than an amplitude threshold value
(Continued)

established for each ultrasonic time signal: The detected amplitude values are assigned to values describing the size and the number of the particulate components.

13 Claims, 3 Drawing Sheets

(51) Int. Cl.
    *G01N 15/02*     (2006.01)
    *G01N 15/06*     (2006.01)
    *G01N 15/10*     (2006.01)
    *G01N 29/032*     (2006.01)
    *G01N 29/44*     (2006.01)
    *G01N 29/48*     (2006.01)
    *G01N 29/24*     (2006.01)
    *G01N 29/22*     (2006.01)

(52) U.S. Cl.
    CPC ......... *G01N 29/032* (2013.01); *G01N 29/221* (2013.01); *G01N 29/222* (2013.01); *G01N 29/228* (2013.01); *G01N 29/2462* (2013.01); *G01N 29/4427* (2013.01); *G01N 29/4454* (2013.01); *G01N 29/48* (2013.01); *G01N 33/205* (2019.01); *G01N 2015/0687* (2013.01); *G01N 2015/1087* (2013.01); *G01N 2291/015* (2013.01); *G01N 2291/0252* (2013.01); *G01N 2291/02416* (2013.01); *G01N 2291/044* (2013.01); *G01N 2291/045* (2013.01); *G01N 2291/101* (2013.01); *G01N 2291/102* (2013.01); *G01N 2291/105* (2013.01)

(56) References Cited

OTHER PUBLICATIONS

J W Griffin et al: "Under-Sodium Viewing: A Review of Ultrasonic Imaging Technology for Liquid Metal Fast Reactors", Mar. 1, 2009 (Mar. 1, 2009).

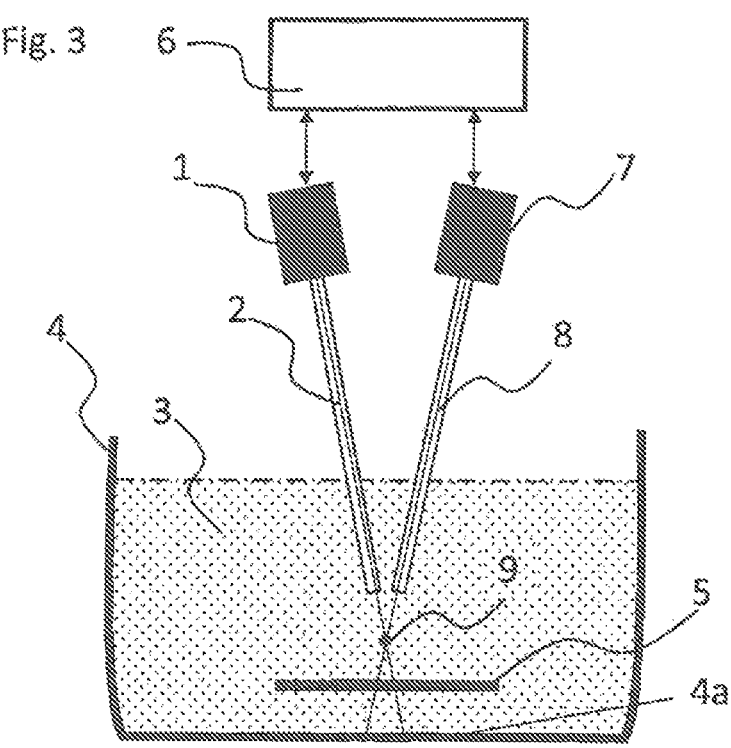
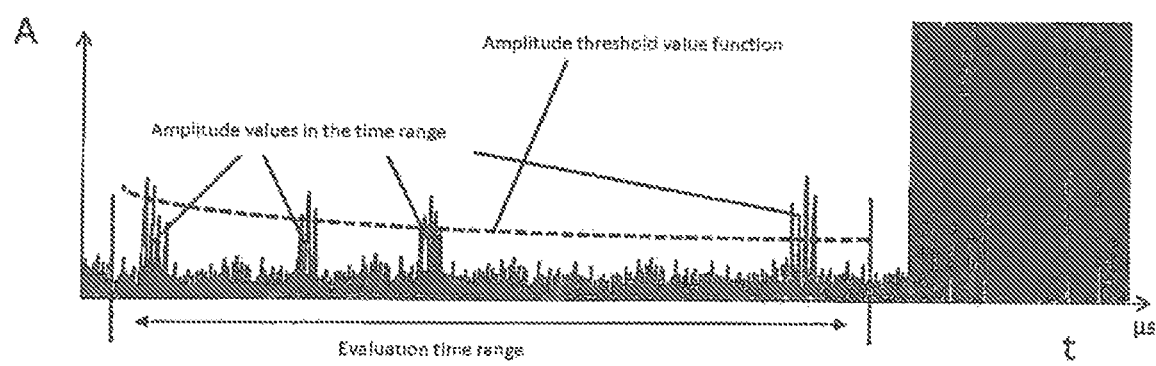

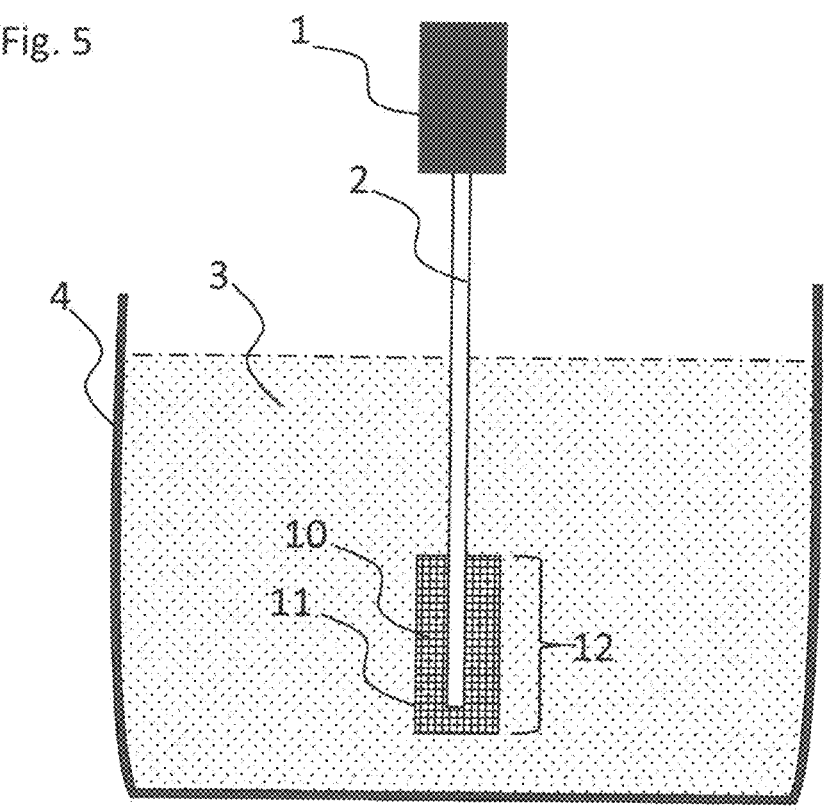

METHOD, DEVICE AND USE FOR THE DEVICE FOR QUANTITATIVELY DETERMINING THE CONCENTRATION OR PARTICLE SIZE OF A COMPONENT OF A HETEROGENEOUS MATERIAL MIXTURE

CROSS REFERENCE TO RELATED APPLICATIONS

Reference is made to PCT/EP2017/058242 filed Apr. 6, 2017, and German Application No. 10 2016 007 173.7 filed Jun. 14, 2016, which are incorporated herein by reference in their entirety.

BACKGROUND OF THE INVENTION

Field of the Invention

The invention relates to a method and a device for quantitatively determining the number and size of particulate components contained in a medium flowing along a flow channel, wherein ultrasonic waves are coupled into the flowing medium, which are reflected at least partially by the particulate components and the reflected ultrasonic wave portions are detected as ultrasonic time signals, on which the quantitative determination is based.

Description of the Prior Art

Especially in the metal processing and chemical industries, it is often necessary to perform a quantitative analysis in particular for heterogeneous material mixtures such as suspensions. Examples are molten metals, which contain contaminants and/or other desirable or undesirable components besides the metal or metal mixtures, which for example may be particles in molten metals of oxides, chlorides, carbides, nitrides, borides and/or intermetallic phases. In the chemical industry, heterogeneous material mixtures are created for example during polymerization when manufacturing polymers. In both examples, it is desirable to be able to make precise quantitative statements about the components of a material mixture, for, determining the number of particles, particle concentration and/or particle sizes, in order to control, adjust or monitor production processes.

In the field of ultrasound-based particle detection, in aluminium melt for example, the "MetalVision" method is known from Kurban M., Sommerville I. D., Mountford N. D. G., Montford P. H., An ultrasonic sensor for the Continuous Online Monitoring of the Cleanliness of Liquid Aluminium, Light Metals 2005, TMS, 945-949, and is used in continuous aluminium casting. In this method, ultrasound is coupled into the liquid aluminium melt via parallel steel waveguides. The lack of reproducibility of the measurement result is disadvantageous.

A method and a device for individual visualization, size measurement and counting of suspended inclusions in a metal melt in a container by use of ultrasound is described in EP 1 194 772 B1 and DE 600 01 951 T2. With at least one ultrasonic transducer, ultrasonic waves are generated in the form of individual "ultrasonic shots" which are coupled via a waveguide into the molten metal that is to be investigated, where they are partially reflected by the inclusions contained in the molten metal. The reflected ultrasonic waves are detected by use of an ultrasonic wave detector and evaluated for purposes of counting as well as measuring and visualization by image analysis. The image analysis and the quantitative measurement of the echo signals obtained from the detected ultrasonic waves are based on a calibration curve which has been obtained as part of a calibration step in which at least one calibration reflector of known, stable size is used. For this purpose, the calibration reflector is positioned in the molten metal in the area of the "focal spot" in which the ultrasonic waves interact with the molten metal and from which reflected ultrasonic wave portions exit and can be captured by at least one ultrasound detector. The calibration curve creates a functional relationship between the amplitudes of detected echo signals and the diameters of the obstructions by which the echo signals have been reflected.

SUMMARY OF THE INVENTION

The invention is a method and device, and use thereof, for the purpose of determining a number of particles, a particle concentration and/or particle sizes in material mixtures, liquids, suspensions, particularly melts with a high degree of accuracy and reproducibility. It is further intended to reduce the effort associated with the method and the technical features of the device.

The method according to the invention enables the ultrasonic waves to be propagated or coupled directly into the flowing medium, so that at least some of the ultrasonic waves coupled to the flowing medium are reflected by a wall region of a container which limits the flowing medium or by a reflector positioned inside the container, and by which an echo-ultrasonic time signal is generated which can be assigned as a calibration reference to the wall region or the reflector. The ultrasonic waves are preferably coupled into a molten metal in which it is important to detect particulate components quantitatively. It is also possible to perform an analysis of any heterogeneous liquid material mixtures, such as suspensions, by coupling in ultrasonic waves to the flowing medium to enable a quantifying determination of particulate components.

The ultrasonic waves are preferably coupled into the flowing medium which has a main direction of propagation directed at an angle to the direction of flow of the flowing medium. The ultrasonic waves travelling along the main direction of propagation, which are preferably orthogonal to the wall of the container and upon striking the wall are reflected thereby accordingly. The ultrasonic wave portions reflected along the entire ultrasound travel path in the flowing medium, including the ultrasonic waves reflected on the wall region representing the rearward limit thereof in the main direction of propagation are detected preferably in the region of or precisely at the location where the ultrasonic waves are coupled into the flowing medium. In this way, ultrasonic time signals are received along the entire path between the coupling site of the ultrasonic waves into the flowing medium and the rear limit wall. The reflection of ultrasonic waves caused by the wall is distinctive and is a characteristic echo-ultrasonic time signal which provides a reference signal that is used to calculate at least one amplitude threshold function, which defines an amplitude threshold for each detected ultrasonic time signal.

When for example two or more waveguides are used with at least a second waveguide serving as a receiver, the detection location may differ from the coupling location.

An additional reflector having a smooth, preferably flat, reflector surface is inserted into the flowing medium when the distance between the coupling location of the ultrasonic waves and the wall region that limits the flow channel is too great and/or the wall is not suitable for reflecting ultrasonic waves with as little loss as possible, due for example to deposits.

Preferably, at least one of the following physical properties is considered in the calculation of the at least one amplitude threshold function:
a) the ultrasonic field distribution within the flowing medium, that is, the spatial extent and intensity of the ultrasonic waves propagating within the flowing medium as a function of their direction, for example in the form of primary and side lobes;
b) the acoustic attenuation of the ultrasonic waves in the flowing medium, that is, the medium-specific and medium-related reduction of the ultrasonic wave amplitudes with progressive propagation in the flowing medium;
c) the coupling conditions of the ultrasonic waves in the flowing medium, that is, the performance of the transformation of the initial ultrasonic wave energy, from which ultrasonic waves are generated, for example by use of an ultrasonic piezo transducer in the ultrasonic waves propagating inside the flowing medium. In this way, changing coupling conditions are expressed directly as a varying echo-ultrasonic time signal whose direct influence on the amplitude threshold function has an effect on the amplitude threshold values of all ultrasonic time signals. In this case, the amplitude threshold functions are corrected for all temporally subsequent ultrasonic time signals. However, the temporally preceding amplitude threshold values do not have to be corrected.

For purposes of the quantitative capture and evaluation of particulate components contained in the flowing medium, in a further step all amplitude values assigned to the individual captured ultrasonic time signals that are individually larger than an amplitude threshold value defined for the respective ultrasonic time signals are detected or captured.

Advantageously, not all ultrasonic time signals that are generated by reflection events within the flowing medium between the coupling location and the rear wall rear wall region are included for further evaluation. Rather, an evaluation time range is defined that corresponds to a spatial measurement region in the flowing medium along the main direction of propagation and may be located at any point between the coupling location and rear wall that delimits the flow channel. The evaluation time range and the measurement volume for analysis associated therewith may be dimensioned suitably depending on the parameters of the investigation.

In its simplest form, the amplitude threshold value function required for the evaluation of the ultrasonic time signals within a definable evaluation time range is a horizontal straight line on which the detected ultrasonic time signals are superimposed suitably for numerical comparison.

The aspects described previously such as ultrasonic field distribution, attenuation, coupling conditions or the like may be considered correspondingly in the amplitude threshold value function depending on the requirements applicable to the subsequent evaluation of the ultrasonic time signals.

Likewise, the plot of the amplitude threshold value function may follow a logarithmic or exponential course. The acoustic attenuation of the flowing medium follows an exponential function with a negative exponent, for example. In this way, the influence of attenuation may be corrected by multiplying the amplitude threshold value function with an exponential function that has a positive exponent.

Alternatively to or in combination with the aforementioned attenuation correction, the curve of the amplitude threshold value function may be selected as linear with a positive or negative slope. For example, starting from a flat circular oscillator, the sound pressure decreases by approximately $1/z$ with increasing distance $z$ from the location where the ultrasonic waves are coupled into a medium, that is the far field. Accordingly, this influence can be corrected by multiplying the amplitude threshold value function with a function with a positive gradient.

It is also possible to couple the ultrasonic waves into the flowing medium in focused manner. That is, the ultrasonic waves are focused on a focal point located along the main direction of propagation, which is always in front of the wall of the container in the main direction of propagation.

In principle, the focal point may be in any position relative to the evaluation time range and/or the defined measurement volume, that is, it may be selected either inside or outside the evaluation time range.

On the other hand, if the ultrasonic focus is within the evaluation time range, it is advantageous to define the lowest amplitude threshold at the focal point, which then increases on both sides with increasing distance from the focal point. However, if the ultrasound focus is located outside of the evaluation time range, it is advantageous that the amplitude threshold function has a positive or negative gradient.

In general, the plot of the amplitude threshold value function can assume an extremely complex course when multiple influencing variables are considered. It is also helpful to apply several different amplitude threshold value functions, to be able to determine particle size distributions accordingly, for example. A manageable number of different amplitude threshold value functions is typically in the range from 1 to 10.

After capturing all of the amplitude values within the evaluation time range lying above the amplitude threshold value function on the basis of their respective values, finally values describing the size and/or number of the captured or detected particulate components within the flowing medium must be assigned to these amplitude values.

Thus, the number of captured or detected particulate components may be determined on the basis of the number or statistical frequency with which the amplitude values captured per ultrasonic time signal lie above an amplitude threshold value defined for each ultrasonic time signal by the amplitude threshold value function.

On the other hand, the information on size of the particulate components is based on the numerical sum of the amplitude value of the ultrasonic time signal, that is the peak height or amplitude size of an ultrasonic time signal describes the respective particle size. In this context, it should be noted that the peak heights of the ultrasonic time signals are also dependent on the ultrasound coupling conditions, and this consideration must be addressed with a dynamic adaptation of the amplitude threshold value function.

On the basis of the information obtained in this way, it is possible to determine the number of particles and the relative particle size distribution of the particulate components captured in the flowing medium.

If it is necessary to specify the particle sizes exactly in absolute values, reference tables, also called "lookup tables" may be used. It is also possible to determine calibration values or calibration functions in separate test series by capturing ultrasonic time signals, particularly their amplitudes or/and signal shapes, which are obtained by reflection of the ultrasonic waves from a known ultrasonic reflector. The calibration values or calibration functions obtained in this way may subsequently be used as the basis for determining the at least one amplitude threshold value function.

In addition, a device for quantitatively determining the number and size of particulate components contained in a medium flowing along the flow channel is characterized in that in order to couple ultrasonic waves into the flowing medium at least a section of at least one waveguide which is coupled acoustically to an ultrasound transducer which is immersed in the flowing medium. The waveguide mode from a waveguide material is surrounded by an outer layer at least in the region thereof which is immersed in the flowing medium, so that the outer layer is arranged between the other waveguide material and the flowing medium. The outer layer has a material composition which differs from that of the other waveguide material.

The waveguide preferably has a waveguide tip which is blunt, tapered or deliberately geometrically shaped on one side for coupling focused ultrasonic waves into the flowing medium. In this context, at least a portion of the waveguide tip is surrounded by the outer layer, whose material composition is selected depending on the flowing medium in such manner that the material composition dissolves upon contact with the flowing medium.

The material composition of the outer layer contains at least one substance which initiates and/or supports the wetting of the flowing medium on the waveguide material, and which is not the same as the flowing medium. The at least one substance is preferably a smelting salt.

In order to bring the smelting salt decisively into the region of the waveguide tip at least for use in a molten metal, it is surrounded by a material that melts and/or dissolves in the measurement medium, such as an aluminium foil. The smelting salt brought into contact with the waveguide tip displaces any oxides on the surface of the waveguide, thus enabling direct contact between the waveguide and the flowing medium, preferably in the form of an aluminium melt.

Further details are given in the following description with reference to the following embodiments.

BRIEF DESCRIPTION OF THE DRAWINGS

In the drawing:

FIG. 3 shows the device according to FIG. 2 with two waveguides for coupling focused ultrasonic waves into the medium;

FIG. 4 is a diagrammatic representation of ultrasonic time signals having a superimposed amplitude threshold value function and evaluation time range; and FIG. 5 shows the device according to FIG. 1 with a waveguide with a wetting shoe on the waveguide tip.

DETAILED DESCRIPTION OF THE INVENTION

With reference to the above drawings, which will be described in the following text, a device is described with which it is possible to measure at least one of concentration and number and size of particulate components in a flowing medium 3. The medium may for example be material mixtures, melts, molten metals, such as aluminium melt, or liquids which are measured with a high degree of accuracy.

Figure 1:
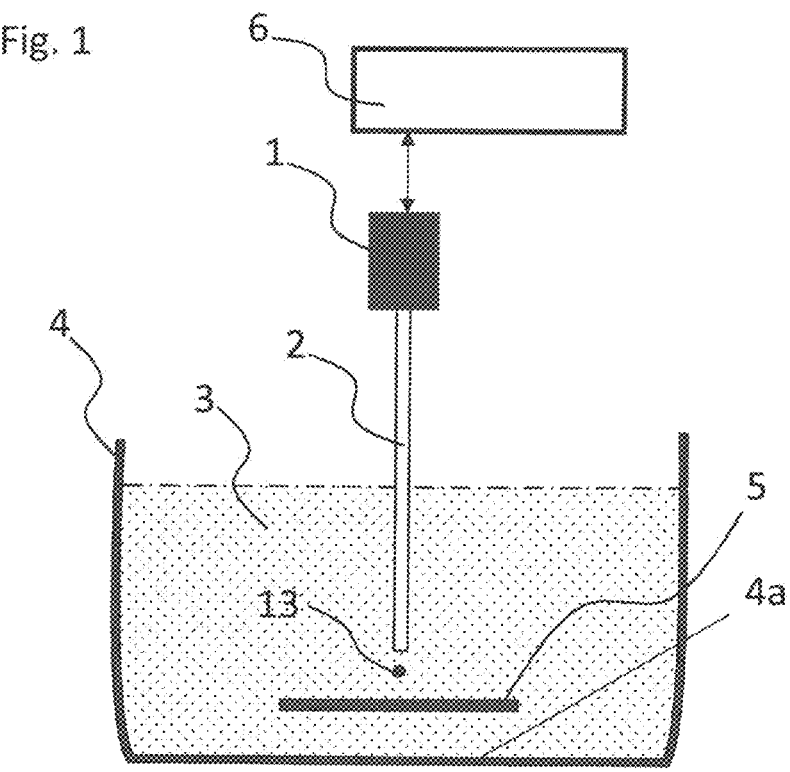
FIG. 1 shows a device for measuring particulate components in a flowing medium by use of a waveguide for coupling ultrasonic waves into the medium.

As represented FIG. 1, ultrasound is generated by an ultrasonic transducer 1, which functions as an emitter and is coupled into the liquid to be investigated via a waveguide 2, which is a means for coupling the ultrasound to the liquid. It is assumed that the flowing medium 3 flows through the container 4 in a direction which is orthogonal to the plane of the drawing. As represented in FIG. 1, the same ultrasonic transducer 1 may also serve as the receiver of the ultrasonic waves from the flowing medium 3.

Figure 2:
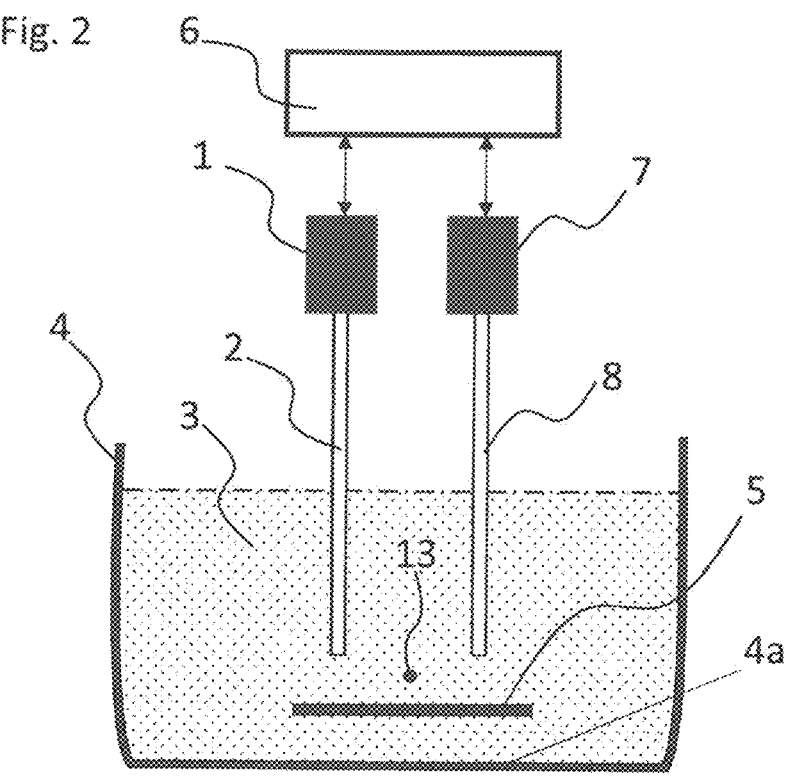
FIG. 2 shows the device according to FIG. 1 with two waveguides for coupling ultrasonic waves into the medium.

In each of FIG. 2 and FIG. 3, a further ultrasonic transducer 7 is used with an additional acoustically coupled waveguide 8. The waveguide 8 couples the additional ultrasonic transducer 7 acoustically with the flowing medium 3. If more than one ultrasonic transducer is present, various operating modes can be implemented. For example, the ultrasonic transducer 1 may serve as the emitter and the ultrasonic transducer 7 may serve as the receiver, or vice versa, or both ultrasonic transducers 1, 7 may serve as emitters and operate with a time offset as receivers. The ultrasonic signals received by at least one ultrasonic transducer 1,7 are recorded and evaluated by the measurement devices/evaluation technology/evaluator 6. The evaluator 6 captures the reflections or echoes of the ultrasonic field from the flowing medium 3 and the reflection from an ultrasonic reflector 5 optionally introduced into the flowing medium 3. A limit wall region 4a of the container 4, which at least partially encloses the material mixture, preferably serves as an ultrasonic reflector 5, delimiting the ultrasonic waves in the direction of propagation thereof. The echo of the ultrasonic signals reflected by the limit wall 4a is used to calibrate the echoes from the flowing medium 3. For at least one amplitude threshold value function, which is defined based on the reflector from limit wall 4a, is used to evaluate the reflections from the flowing medium 3.

A preferred device among other elements of the at least one ultrasonic transducer 1 includes waveguide 2 coupled acoustically to the ultrasonic transducer 1, a container 4 for holding or allowing a flowing medium 3, particularly a suspension, to pass through, an ultrasonic reflector 5 or wall region 4a arranged in the medium, wherein the waveguide 2 protrudes into the medium 3 and is arranged in such manner relative to the ultrasonic reflector 5 and the wall region 4a so that an ultrasonic field formed in the medium 3 has at least one focus 13, which lies spatially between the ultrasonic reflector 5, wall 4a, and the first waveguide 2 and/or an additional waveguide 8.

A further preferred device has, among other elements, at least one evaluator 6 coupled with the at least one ultrasonic transducer 1, the waveguide 2 coupled acoustically to the ultrasonic transducer 1, a container 4, through which passes a flowing medium 3 particularly in the form of a suspension. The waveguide 2 protrudes into the medium 3 and is configured to couple an ultrasonic field generated by the ultrasonic transducer 1 into the medium 3 and to couple reflections of the ultrasonic field on boundary surfaces in the flowing medium 3 particularly on particles in the medium 3, into the ultrasonic transducer as ultrasonic time signals. The evaluator is configured to capture and count at least one of energy maxima and power maxima in the reception time signal using a threshold function.

A further preferred device has at least the at least one waveguide 2 coupled acoustically to the ultrasonic transducer 1, which protrudes into a flowing medium that is to be analyzed, particularly a suspension, wherein at least part of the waveguide 2 has an outer layer 10 with a material composition that differs from the rest of the waveguide material. The outer layer 10 is arranged between the rest of the waveguide material and the flowing medium 3 as shown in FIG. 5.

The space, that is defined by the end of the at least one waveguide 2 and the ultrasonic reflector 5 and wall 4a, serves as the measurement volume.

A focus 13 of the ultrasonic field is preferably located within the measurement volume.

The echo reflection created by the ultrasonic reflector 5 and wall 4a is also referred to as the rear wall echo or reflection. These two terms are interchangeable.

The ultrasonic reflector 5 integrated in the construction generates a rear wall reflection in the ultrasonic signal as shown in FIG. 4. The rear wall reflection is used for a calibration of the ultrasonic signal, since the coupled ultrasonic energy is represented herein. The calibration relates to absolute particle size which is included in the definition of the amplitude threshold value function. The rear wall echo or reflection may also be used to test the function of the measurement system, since coupling fluctuations in the ultrasound can be detected by waveguides in the liquid and also corrected thereby.

The positioning of the ultrasonic reflector inside the measurement medium is determined by the waveguides that are used. In this context, the following arrangements are preferably possible:

a) If the waveguides are arranged at an angle relative to each other (FIG. 3), the highest ultrasound amplitude is achieved by focus 9, which results from the intersection point between the extension of the two waveguides. The ultrasonic reflector is arranged at such a distance from the waveguide that the focus 9 is located between the waveguide on the one side and the ultrasound reflector on the other side. The distance between the focus 9 and the ultrasonic reflector is preferably in the range from 5 mm to 80 mm.

In the event that container 4 is only very shallow, the focus 9 is more distant than the reflector 5, that is the container wall. Although this case is not ideal, it is still possible to carry out a measurement.

b) If the waveguides 2, 8 are arranged parallel to each other (FIG. 2) or if a single waveguide 2 is being used (FIG. 1), the position of the ultrasonic reflector 5 and wall region 4a is defined by the focus 13 of the ultrasonic field. This focus 13 is dependent on the geometry of the tips of the waveguides 2, 8, which are located in the flowing medium 3. The ultrasonic reflector 5, that is the wall 4a of the container is preferably arranged at a greater or equal distance (13). Even when the construction is as represented in FIG. 1 and/or FIG. 2, the focus 13 of the ultrasonic field is located in a space that is limited on the one hand by the tips of the waveguides and on the other by the ultrasonic reflector 5 that is the limit wall 4a of the container.

In the event that container 4 is only very shallow, the focus 9 may be more distant than the reflector 5, which is the wall of the container. Although this case is not ideal, it is still possible to carry out a measurement.

c) Depending on the size or depth of the container 4, the focus 13 may also lie behind the reflector 5 or behind the wall 4a in the direction of ultrasonic propagation, even outside the container 4, for example.

In order to measure an aluminium melt as a flowing medium 3, a structure according to FIG. 3, for example may be selected. Focus 9 corresponds approximately to a distance of 50 mm from the tips of the waveguides 2, 8. The angle between the waveguides 2,8 in this case is equal to 8 to 30°. The ultrasonic reflector 5 or the limit wall 4a of the container is manufactured from a hot working steel. In this context, particularly ceramic materials and/or all hot-melting materials which are poorly wetted in the flowing medium are also highly suitable for use, including for example SiAlON, silicon nitride, aluminium oxide.

The waveguides 2,8 are preferably selected such that sufficient wetting of the flowing medium is produced. The waveguide setups correspond for example to those shown in FIGS. 1, 2, 3, 5.

For the aluminium melts as the medium, waveguides of titanium (grade 2) may be used. Further suitable waveguide materials are silicon nitride, SiAlON, steel (hot working steel 1018 H13 (USA) or X40 CrMoV 5-1 and annealed steel (1.4436)). The waveguides are for example 600 mm, 500 mm, 400 mm or 300 mm long and have diameters of 8 mm, 9 mm. 10 mm, 11 mm, 12 mm, 13 mm or 14 mm.

The frequency of the ultrasonic field is preferably in the frequency range from 2 MHz to 12 MHz. For example, for an aluminium melt as the measurement medium, an ultrasound frequency of 6 MHz or 10 MHz has proven suitable, wherein an ultrasound frequency of about 10 MHz is particularly preferred.

In order to evaluate the number of particles in the flowing medium, an evaluation time range according to FIG. 4 before the rear wall echo or ultrasonic reflector echo is selected. The selection of the evaluation time range enables the measurement volume to be adjusted individually. A smaller evaluation time range corresponds to a smaller measurement volume.

In this case, the evaluation time range is coupled to the ultrasonic fields in the medium very powerfully, because sufficient ultrasound energy is needed.

For the aluminium melts, an evaluation time range is selected that corresponds approximately to 4 cm in the medium. The end of the evaluation time range is located just in front of the rear wall echo (FIG. 4). Since the measurement volume can be adjusted with this time range, in principle a considerably shorter time range and, given sufficient ultrasonic energy, a considerably longer time range are also possible.

Counting is preferably carried out of the number of amplitude values which exceed a given amplitude threshold value function within the selected time range (see FIG. 4). The count value is proportional to the particle concentration, so that a specific particle concentration may be calculated from the count value with the aid of a calibration function.

For an aluminium melt, the relevant concentration ranges that can also be captured by a measuring system, are detectable in the range from 100 particles to 100,000 particles per kg aluminium melt.

The amplitude threshold value function or the selection of multiple amplitude threshold value functions enable a conclusion to be drawn regarding at least one of the particle size and particle size distribution. The height and shape of the rear wall echo can be used for calibration purposes. It is also possible to draw a conclusion about at least one of the absolute particle size and particle size distribution. Otherwise, a qualitative conclusion is obtained. The amplitude threshold value function may also be coupled mathematically to the rear wall echo to correct coupling fluctuations from at least the coupling and the receiving medium into the flowing medium.

The amplitude threshold value function preferably has a constant temporal curve. But in order to correct the acoustic attenuation in the measurement medium for example, a logarithmic or exponential curve may be used. The acoustic attenuation follows for example, an exponential function with a negative exponent. The effect of attenuation may be corrected by multiplication with an exponential function having a positive exponent.

The introduction of a wetting shoe (12), shown in FIG. 5, enables the locally controllable wetting of the waveguide with the medium. In such a case, a cover (11) which dissolves in the flowing medium and which contains a substance (10) that promotes wetting, is placed on the tip of the waveguide 2. After immersion in the medium 3, the wetting shoe (12) dissolves and the substance (10) that promotes wetting is released locally. A further option is melting the substance that promotes wetting and immersing one end of the waveguide (2) (8) in a liquid substance (10) that promotes wetting.

The substance (10) that is used preferably promotes wetting for a molten metal and particularly aluminium melt use conventional smelting salts (salt 1: approximate composition: KCl (47.6%), NaCl (45.7%), SO4 (2.14%), CaF2 (0.14%); salt 2: approximate composition: KCl (50%), NaCl (50%)).

The salts may be placed in a cover of aluminium foil, for example, which serves as the outer Layer (11). The cover is then placed over the tips of the waveguides (see FIG. 5) and dissolved in the liquid/molten metal.

The cover may also be made from a material which melts or dissolves in the liquid.

LIST OF REFERENCE SIGNS

1 Ultrasonic transducer
2 Waveguide
3 Liquid, particularly suspension
4 Container
4a Limit wall
5 Ultrasonic reflector
6 Evaluator
7 Further ultrasonic transducer
8 Waveguide
9 Ultrasonic field focus
10 Outer layer
11 Cover
12 Wetting shoe
13 Ultrasonic field focus

The invention claimed is:

1. A method for quantitative determination of a number and size of particulate components contained in a flowing molten metal medium in a container including a wall, wherein ultrasonic waves are coupled into the molten metal flowing medium, are reflected at least partially by the particulate components and reflected ultrasonic waves are detected as ultrasonic time signals which are used for the quantitative determination, comprising steps of:

acoustically coupling the ultrasonic waves into the molten metal flowing medium with an ultrasonic transducer including a waveguide having at least a part of the waveguide immersed in the molten metal flowing medium with at least one portion of the acoustically coupled ultrasonic waves being reflected by the wall of the container containing the molten metal flowing medium or a reflector within the container to provide echo-ultrasonic time signals which are assignable to a wall region or the reflector and are used to provide a calibration reference, the ultrasonic waves being coupled into the molten metal flowing medium flowing through the container in a main direction of propagation at an angle relative to a direction of flow of the molten metal flowing medium, the ultrasonic waves flowing in the molten metal flowing medium being focused at a focal point located along the main direction of propagation of the molten metal flowing medium which is located either before or after the reflector or the wall of the container with the ultrasonic waves propagating along the main direction of propagation impinging orthogonally or at an angle on the container and are reflected;

detecting the reflected ultrasonic waves at a location of coupling of the ultrasonic waves into the molten metal flowing medium;

determining at least one amplitude threshold value function for establishing an amplitude threshold value for the detected reflected ultrasonic time signals with the at least one amplitude threshold being based on at least the calibration reference;

detecting amplitude values associated with individual ultrasonic time signals which are greater than the at least one amplitude threshold value for the reflected ultrasonic time signals; and processing the detected amplitude values to provide a number and size of the particulate components.

2. The method according to claim 1, wherein the determined at least one amplitude threshold value relates to one of the following physical properties:

an ultrasonic field distribution in the molten metal flowing medium;

acoustic attenuation in the ultrasonic waves in the molten metal flowing medium; and coupling conditions of the ultrasonic waves into the molten metal flowing medium.

3. The method according to claim 1, wherein amplitude values of individual reflected ultrasonic time signals which are larger than the determined amplitude threshold value are detected within a defined evaluation time range, corresponding to a spatial measurement range within the molten metal flowing medium along the main direction of propagation and the spatial measurement range is located between the location of coupling the ultrasonic waves into the molten metal flowing medium and the wall of the container or the reflector.

4. The method according to claim 2, wherein amplitude values of individual reflected ultrasonic time signals which are larger than the determined amplitude threshold value are captured within a defined evaluation time range, corresponding to a spatial measurement range within the molten metal flowing medium along the main direction of propagation and the spatial measurement range is located between the location of coupling the ultrasonic waves into the molten metal flowing medium and the wall of the container or the reflector.

5. The method according to claim 2, further comprising assigning detected amplitude values to the wall region or the reflector with the values being used to provide a calibration reference for identifying particulate components within the molten metal flowing medium is based on a number or a statistical frequency of detected amplitude values per ultrasonic time signal which are above the at least one amplitude threshold value defined for each ultrasonic time signal by the at least one amplitude threshold value function.

6. The method according to claim 3, further comprising assigning detected amplitude values to values being used for identifying a number of particulate components within the molten metal flowing medium is based on a number or a statistical frequency of detected amplitude values per ultrasonic time signal which are above the at least one amplitude threshold value defined for each ultrasonic time signal by the at least one amplitude threshold value function.

7. The method according to claim 4, further comprising assigning detected amplitude values to the wall region or the reflector with the values being used to provide a calibration reference for identifying particulate components within the molten metal flowing medium is based on a number or a statistical frequency of detected amplitude values per ultrasonic time signal which are above the at least one amplitude threshold value defined for each ultrasonic time signal by the at least one amplitude threshold value function.

8. The method according to claim 1, wherein the assigning of the detected amplitude values to the size of the particulate components is based on a numerical value of amplitude of the ultrasonic time signals.

9. The method according to claim 8, comprising: obtaining absolute size values based on a calibration value or a calibration function with the calibration value or the calibration function being obtained by reflection of ultrasonic waves from the ultrasonic reflector.

10. The method according to claim 9, wherein the determining of the at least one amplitude function comprises calculating the at least one amplitude threshold value function by using the calibration value or the calibration function.

11. A device for providing a quantitative determination of a number and size of particulate components contained in a molten metal flowing medium in which ultrasonic waves are coupled into the molten metal flowing medium and are reflected by the particulate components and the reflected ultrasonic waves are detected as ultrasonic time signals on which the quantitative determination is based, comprising:
- an acoustic coupling for coupling ultrasonic waves into the molten metal flowing medium by using at least one acoustic waveguide which is coupled to an ultrasound transducer which is immersed in the flowing molten metal medium;
- the waveguide includes an outer layer which is at least in a region immersed in the molten metal flowing medium;
- the outer layer is positioned between a layer of the at least one waveguide and the molten metal flowing medium; and wherein
- a material of the outer layer contains at least one substance which is a smelting salt which functions to at least initiate and support wetting of the waveguide with the molten metal flowing medium, and wherein
- the waveguide is surrounded by a cover or a matrix of material that melts in the molten metal flowing medium.

12. The device according to claim 11, wherein:
the waveguide includes an end having at least one of a blunt, tapered or geometrical shape which on one side focuses ultrasonic waves into the flowing medium.

13. A use of the device according to the device of claim 11, comprising determining a concentration of foreign bodies in the molten metal flowing medium.

* * * * *